120; 4,045,478

United States Patent [19]
Umemura et al.

[11] 4,045,478
[45] Aug. 30, 1977

[54] METHOD FOR THE PREPARATION OF METHACRYLIC ACID

[75] Inventors: Sumio Umemura; Kyoji Ohdan; Kenichi Suzuki; Fumio Adachi, all of Ube, Japan

[73] Assignee: Ube Industries, Ltd., Ube, Japan

[21] Appl. No.: 658,909

[22] Filed: Feb. 18, 1976

[30] Foreign Application Priority Data

Feb. 28, 1975 Japan .................................. 50-23904
Mar. 12, 1975 Japan .................................. 50-29117

[51] Int. Cl.$^2$ ............................................. C07C 51/32
[52] U.S. Cl. ............................ 260/530 N; 252/432; 252/435; 252/437; 260/530 R
[58] Field of Search ................... 260/530 N; 252/437, 252/435, 432

[56] References Cited
U.S. PATENT DOCUMENTS

| | | | |
|---|---|---|---|
| 3,686,294 | 8/1972 | Ito et al. | 260/530 N |
| 3,865,873 | 2/1975 | Oda et al. | 260/530 N |

*Primary Examiner*—Vivian Garner
*Attorney, Agent, or Firm*—Miller & Prestia

[57] ABSTRACT

Methacrylic acid can be produced from methacrolein with a high reaction percentage of methacrolein and a high selectivity percentage of methacrylic acid, by bringing a reaction feed containing methacrolein and molecular oxygen into contact with an oxidation catalyst at a temperature of 200 to 450° C, the oxidation catalyst comprising oxides of molybdenum, phosphorus, calcium, at least one element selected from the group consisting of arsenic, bismuth, tin, titanium, tantalum and boron and, optionally, at least one element selected from the group consisting of antimony, niobium and magnesium.

10 Claims, No Drawings

METHOD FOR THE PREPARATION OF METHACRYLIC ACID

The present invention relates to a method for the preparation of methacrylic acid. More particularly, the present invention relates to a method for the preparation of methacrylic acid by catalytically oxidizing methacrolein in vapor phase with molecular oxygen at an elevated temperature.

Various methods are known for the preparation of unsaturated aliphatic carboxylic acids, for example, acrylic acid and methacrylic acid, by catalytically oxidizing unsaturated aliphatic aldehydes, for example, acrolein and methacrolein, in vapor phase with molecular oxygen in the presence of an oxidation catalyst at an elevated temperature. In these conventional methods, the major methods relate to the production of acrylic acid and the minor methods concern the preparation of methacrylic acid. Broadly, it is known that when the conventional oxidation catalyst is applied to the oxidation of methacrolein into methacrylic acid, the percentage of selective conversion of the oxidized methacrolein into the methacrylic acid is smaller than that of the acrolein into acrylic acid when the same catalyst as mentioned above is applied to the oxidation of acrolein. It is also known that when the conventional oxidation catalyst which is useful for the conversion of acrolein into acrylic acid is utilized to oxidize the methacrolein into methacrylic acid, the percentage of selective conversion of the oxidized methacrolein into methacrylic acid is relatively low. The difference in the catalytic effect of the conventional oxidation catalyst between the oxidation of acrolein and the oxidation of methacrolein seems to be derived from the difference in molecular structures between acrolein and methacrolein. Methacrolein has a branched atomic group from a backbone atomic group thereof, while acrolein has no branched atomic group. Due to the branched atomic group, the oxidation of methacrolein is more difficult than that of acrolein. One attempt to oxidize methacrolein is contained in Japanese Patent Application Publication No. 10308/1960 which discloses a new oxidation catalyst consisting of oxides of molybdenum and phosphorus, that is, Mo-P-O type. This type of catalyst is effective to oxidize both acrolein and methacrolein. However, when this type of catalyst is utilized for oxidizing methacrolein to prepare methacrylic acid, the percentage of selective conversion of the oxidized methacrolein into methacrylic acid is relatively low, that is about 44%, as indicated in Example 5 in the above Publication.

Under these circumstances, a new catalyst capable of oxidizing methacrolein into methacrylic acid with a high percentage of selective conversion of the oxidized methacrolein into methacrylic acid, is desired.

As a result of various studies, the inventors have discovered that in the Mo-P-O type catalyst, the addition of catalytic calcium ingredient thereto is effective to improve the percentage of selective conversion of the oxidized methacrolein into methacrylic acid. Further, it was discovered by the inventors that the addition of at least one catalytic ingredient selected from the group consisting of arsenic, bismuth, tin, titanium, tantalum and boron, to the Mo-P-Ca-O type catalyst, is highly effective to improve both the percentage of reaction of methacrolein and the percentage of selective conversion of the oxidized methacrolein into methacrylic acid. The present invention has been developed on the basis of the above-mentioned discoveries.

An object of the present invention is to provide a method for the preparation of methacrylic acid by oxidation of methacrolein with a high percentage of selective conversion of the oxidized methacrolein into methacrylic acid.

The other object of the present invention is to provide a method for the preparation of methacrylic acid by using an oxidation catalyst which is capable of converting methacrolein into methacrylic acid with a high percentage of selective conversion of the oxidized methacrolein into methacrylic acid and with a high reaction percentage of methacrolein. The percentage of selective conversion of the oxidized methacrolein into methacrylic acid used above is expressed by the term "selectivity percentage of methacrylic acid" hereinafter.

The objects mentioned above can be accomplished by the method of the present invention, which comprises bringing a reaction feed containing methacrolein in vapor phase and molecular oxygen into contact with an oxidation catalyst comprising oxides of molybdenum, phosphorus, calcium and at least one element selected from the group consisting of arsenic, bismuth, tin, titanium, tantalum and boron, at a temperature of 200° to 450° C.

In the method of the present invention, the oxidation catalyst may consists of an oxide composition of the formula (I):

$$Mo_aP_bCa_cX_dO_e \qquad (I)$$

wherein X represents at least one member selected from the group consisting of arsenic, bismuth, tin, titanium, tantalum and boron atoms, the subscripts $a$, $b$, $c$ and $d$ respectively denote the numbers of the respective element atoms, said numbers being within the ranges, $a = 5$ to 15, $b = 1$ to 3, $c = 0.1$ to 3 and $d = 0.1$ to 3, and the subscript e represents the number of oxygen atoms which corresponds to the oxides formed from the above-mentioned elements and satisfies the average valency of the elements, said number e being within the range of 16 to 60.

As is mentioned above, the catalyst usable for the method of the present invention may be an oxide composition in which the catalytic ingredient element atoms are combined with oxygen atoms so as to form simple oxides or complex oxides wherein two or more catalytic ingredient element atoms are combined with each other and with oxygen atoms. Further, in the catalyst, one or more catalytic ingredient elements other than molybdenum may be combined with molybdenum and oxygen so as to form a molybdate salt.

The oxidation catalyst mentioned above can be prepared by any of known type of methods for the conventional oxidation catalyst, for example, by providing an aqueous liquid containing therein a molybdenum-containing compound, a phosphorus-containing compound, a calcium-containing compound and at least one compound selected from the group consisting of arsenic-, bismuth-, tin-, titanium-, tantalum- and boron-containing compounds; evaporating the aqueous liquid to form a solid material, and; calcining the dried solid material at a temperature of 300° to 500° C.

The compounds containing the catalytic ingredient elements may be salts such as nitrate, hydroxides, oxides and acids containing the catalytic ingredient elements.

For example, the sources of molybdenum, phosphorus, calcium, arsenic, bismuth, tin, titanium, tantalum and boron may respectively be ammonium molybdate, phosphoric acid or ammonium phosphate, calcium nitrate, arsenic pentoxide, bismuth nitrate, stannic oxide, titanium dioxide, tantalum pentoxide and boric acid.

In a preferable preparation of the catalyst, a predetermined amount of a molybdate, for example, ammonium molybdate, is dissolved in water at an elevated temperature, for example, 60° C; predetermined amounts of phosphoric acid or ammonium phosphate and a water-soluble calcium salt, for example, calcium nitrate, are dissolved into the solution and, thereafter, predetermined amounts of the salts, hydroxide, oxide or acids of the desired catalytic ingredients are dissolved or suspended into the solution. The resultant solution or suspension is subjected to an evaporation to concentrate it. The concentrated solution or suspension is completely dried to obtain a solid material. The solid material is calcined at a temperature of 300 to 500° C for a period of time sufficient for converting the solid material into an activated catalyst.

One embodiment of the method of the present invention comprises bringing a reaction feed containing methacrolein in vapor phase and molecular oxygen into contact with an oxidation catalyst comprising oxides of molybdenum, phosphorus, calcium, at least one element selected from the group consisting of arsenic, bismuth, tin, titanium, tantalum and boron, and at least one element selected from the group consisting of antimony, niobium and magnesium, at a temperature of 200° to 450° C.

In the above mentioned special embodiment, the oxidation catalyst may consist of an oxide composition of the formula (II):

$$Mo_aP_bCa_cX_fY_gO_e \qquad (II)$$

wherein X represents at least one member selected from the group consisting of arsenic, bismuth, tin, titanium, tantalum and boron atoms, Y represents at least one member selected from the group consisting of antimony, niobium and magnesium, the subscripts $a$, $b$, $c$, $f$ and $g$ respectively denote the numbers of the respective element atoms, said numbers being within the ranges, $a = 5$ to 15, $b = 1$ to 3, $c = 0.1$ to 3, $f = 0.1$ to 3 and $g = 0.1$ to 3, and the subscript $e$ represents the number of oxygen atoms which corresponds to the oxides formed from the above-mentioned elements and satisfies the average valency of the elements, said number $e$ being within the range of 16 to 68.

The oxidation catalyst mentioned above can be prepared by providing an aqueous liquid containing therein a molybdenum-containing compound, a phosphorus-containing compound, a calcium containing compound, at least one compound selected from the group consisting of arsenic-, bismuth-, tin-, titanium-, tantalum- and boron-containing compounds and at least one compound selected from the group consisting of antimony-, niobium- and magnesium- containing compounds; evaporating the aqueous liquid to form a solid material, and; calcining the dried solid material at a temperature of 300° to 500° C.

The compound containing antimony, niobium or magnesium may be salt, hydroxide or oxide thereof. The sources of antimony, niobium and magnesium are preferably, antimony trioxide, niobium pentoxide and magnesium nitrate.

In a preferable embodiment, the method of the present invention may comprise bringing a reaction feed containing methacrolein in vapor phase and molecular oxygen into contact with an oxidation catalyst comprising oxides of molybdenum, phosphorus, calcium, arsenic and at least one element selected from the group consisting of bismuth, tin, titanium, tantalum, boron, antimony, niobium and magnesium, at a temperature of 200° to 450° C.

In the above embodiment, the oxidation catalyst usable for the present invention may consist of an oxide composition of the formula (III):

$$Mo_aP_bCa_cAs_hZ_iO_e \qquad (III)$$

wherein Z represents at least one member selected from the group consisting of bismuth, tin, titanium, tantalum, boron, antimony, niobium, and magnesium atoms, the subscripts $a$, $b$, $c$, $h$ and $i$ respectively represent the numbers of the respective element atoms, the numbers being within the following ranges, $a = 5$ to 15, $b = 1$ to 3, $c = 0.1$ to 3, $h = 0.1$ to 3, and $i = 0.1$ to 3, and the subscript $e$ represents the number of oxygen atoms which corresponds to the oxides formed from the above-mentioned elements and satisfies the average valency of the elements, said number $e$ being in a range of 16 to 68.

The oxidation catalyst mentioned above can be prepared by providing an aqueous liquid containing therein a molybdenum-containing compound, a phosphorus-containing compound, a calcium-containing compound, an arsenic-containing compound and at least one compound selected from the group consisting of bismuth-, tin-, titanium-, tantalum-, boron-, antimony-, niobium- and magnesium-containing compounds; evaporating said aqueous solution to form a solid material, and; calcining the dried solid material at a temperature of 300° to 500° C.

The above-mentioned oxidation catalyst of the present invention may be composed of the catalytic ingredient alone. However, in order to improve the mechanical rigidity of the catalyst, it is preferable that the catalytic ingredient is supported on a carrier. The carrier may consists of any type of conventional carrier material. However, it is preferable that the carrier consists of at least one material selected from the group consisting of diatomaceous earth, silica, alumina, silicon carbide, silica-alumina and water-soluble silica sol. There is no limitation to size and form of the catalyst. That is, the oxidation catalyst of the present invention can be screened into a desired size and can be formed into a desired form, for example, powder, grains, granules, pellets or tablets having a desired rigidity, depending upon the purpose and conditions under which the catalyst is used. Further, it should be noted that the formation of the catalyst results is no change in the catalytic activity of the catalyst.

In the method of the present invention, the reaction feed comprises methacrolein and molecular oxygen. This reaction feed can be prepared by mixing a methacrolein sourse in vapor phase with a molecular oxygen-containing gas. The molecular oxygen-containing gas may be industrially pure oxygen gas. However, it is not required that the molecular oxygen-containing gas have a particularly high concentration of oxygen. Accordingly, the molecular oxygen-containing gas may be air, which is economically advantageous. The molecular oxygen-containing gas can contain an inert gas which does not affect the conversion of methacrolein into methacrylic acid, for example, nitrogen, carbon dioxide and steam. Especially, steam is effective for increasing not only the selectivity percentage of methacrylic acid but the durability in catalytic activity of the catalyst.

The methacrolein source to be used in the method of the present invention is not required to have a high concentration of methacrolein. Accordingly, the sourse of methacrolein may be an oxidation product of isobutylene or an oxidation product of a spent BB which is a residue obtained by separating 1,3-butadiene from $C_4$ fraction which is a by-product from thermally-cracking naphtha. The spent BB contains n-butene and isobutylene. However, it is not preferable that the source of methacrolein contain a large amount of unsaturated aldehydes other than methacrolein therein, because the other aldehydes cause not only a lowering of the reaction velocity but produce a large amount of by-products, and polymerized materials. Accordingly, it is desired that the methacrolein source contain no impurity which will result in an undesirable influence on the conversion of methacrolein into methacrylic acid.

The oxidation catalyst of the present invention may be used in a fluidized bed, moving bed or fixed bed. However, it is most advantageous that the oxidation catalyst is employed in the fixed bed, because in the fixed bed the oxidation catalyst not only can convert methacrolein into methacrylic acid with a high reaction percentage of methacrolein and a high selectivity percentage of methacrylic acid while preventing undesirable side-reactions, but can maintain the catalytic activity thereof at a high level.

The contact of the reaction feed with the oxidation catalyst may be effected under an ambient pressure, increased pressure or red uced pressure. However, it is convenient that the contact be effected under an ambient pressure. The oxidation temperature in the method of the present invention is in a range from 200° to 450° C, preferably, from 250° to 400° C. There is no limitation with regard to the contact time, of the reaction feed with the oxidation catalyst as far as the desired oxidation is completed within the time. However, it is preferable that the reaction feed is kept in contact with the oxidation catalyst for 0.1 to 12 seconds, more preferably, 0.5 to 10 seconds, under an ambient pressure.

In a preferable embodiment of the method of the present invention, the reaction feed contains methacrolein in vapor phase, air and steam. In this reaction feed, it is preferable that the ratio by mole of methacrolein to molecular oxygen is 1:0.5 to 10, more preferably 1:1 to 8, and the ratio by mole of methacrolein to steam is 1:1 to 30, more preferably, 1:2 to 25.

The resultant methacrylic acid from the method of the present invention may be isolated from the oxidation mixture by any conventional isolating method. That is, the resultant methacrylic acid may be isolated by distillation at a temperature of 161° C under a pressure of 760 Torr, or by extraction using, for example n-hexane as an extraction solvent.

The specific examples, shown below will serve to more fully explain the practice of the present invention. However, it should be understood that the examples are only illustrative, and in no way limit the scope of the present invention.

In the examples, the percentage of reaction of methacrolein and the percentage of selection of methacrylic acid were calculated in accordance with the following equations, respectively.

$$\text{Reaction percentage} = \frac{X_1 - X_2}{X_1} \times 100$$

$$\text{Selectivity percentage} = \frac{Y}{X_1 - X_2} \times 100$$

wherein $X_1$ denotes an amount by mole of methacrolein in the reaction feed prior to the start of oxidation, $X_2$ denotes an amount by mole of the residual methacrolein in the oxidation mixture after the completion of oxidation, and Y denotes an amount by mole of the resultant methacrylic acid in the oxidation mixture after the completion of oxidation.

EXAMPLE 1

An oxidation catalyst was prepared using the following procedures. A muddy aqueous suspension of catalytic ingredients was prepared by dissolving 84.75 g of ammonium molybdate [$(NH_4)_6Mo_7O_{24}.4H_2O$] in 200 ml of water which had been heated to a temperature of 60° C and, then, adding 4.6 g of 85% phosphoric acid ($H_3PO_4$), 9.45 g of calcium nitrate ($Ca(NO_3)_2.4H_2O$) and 3.20 g of titanium dioxide ($TiO_2$) into the solution successively in the above-mentioned order. The muddy aqueous suspension was stirred while heating at a temperature of 80° C so that the suspension was concentrated. The concentrated suspension was further concentrated by a drum dryer and, thereafter, completely dried at a temperature of 120° C. A solid material obtained by the above drying, was formed into pellets having a diameter of 5 mm and a length of 5 mm. The pellets were calcined at a temperature of 400° C for 5 hours in a calcining furnace while flowing air through the calcining furnace. The resultant catalyst had an atomic ratio of Mo:P:Ca:Ti of 12:1:1:1.

The oxidation catalyst was crushed into grains and the grains were screened by Tyler Standard screens to collect the grains having a 16 through 28 mesh size.

An oxidation column was prepared by charging a U-shaped glass reaction tube, having an inner diameter of 6 mm, with 5 ml of the oxidation catalyst grains.

An oxidation of methacrolein was carried out using the following procedures. The oxidation column was heated to a temperature of 350° C. A reaction feed containing 2.2% by volume of methacrolein in vapor phase, 10.1% by volume of oxygen, 30.1% by volume of steam and 57.0% by volume of nitrogen, was flowed through the oxidation column at a flow rate of 176 ml/min while maintaining the column at the above-mentioned temperature. The reaction mixture gas was kept in contact with the oxidation catalyst for 1.7 seconds.

It was observed that the reaction percentage of the methacrolein was 68.5 and the selectivity percentage of the resultant methacrylic acid was 76.0. Further, it was observed that small amounts of acetic acid, carbon dioxide and carbon monoxide was by-produced in addition to the methacrylic acid.

EXAMPLES 2 THROUGH 12

Procedures identical to those in Example 1 were repeated eleven times, except that the catalytic ingredient elements in the catalysts were in the atomic ratios indicated in Table 1 and the oxidation temperature and time were as indicated in Table 1. In the preparation of the oxidation catalysts, ammonium molybdate was used as a source of the molybdenum ingredient, phosphoric acid as a source of the phosphorus ingredient, calcium nitrate as a source of the calcium ingredient, antimony trioxide as a source of the antimony ingredient, bismuth nitrate as a source of the bismuth ingredient, tantalum pentoxide as a source of the tantalum ingredient, arsenic pentoxide as a source of the arsenic ingredient and niobium pentoxide as a source of the niobium ingredient. The results are indicated in Table 1.

COMPARISON EXAMPLES 1 THROUGH 6

Procedures identical to those in Example 1 were repeated six times using oxidation catalysts outside the scope of the present invention. The oxidation catalysts used here consisted of the catalytic ingredients in the atomic ratios indicated in Table 1. The oxidation temperature and time were as indicated in Table 1. The results are also indicated in Table 1.

As seen from Table 1, in examples 1, 2, 3 and 6, the reaction percentages of methacrolein are very low, and in Examples 3, 4 and 5, the selectivity percentages of the resultant methacrylic acid are very low.

EXAMPLES 17 THROUGH 19

The same procedures as in Example 1 were repeated three times, except that tin dioxide was used in place of the titanium dioxide and the atomic ratio of Mo : P : Ca : Sn and the oxidation temperature were as indicated in Table 3. The results are also indicated in Table 3.

Table 3

| Item Ex. No. | Atomic ratio | | | | Oxidation temp. (° C) | Reaction percentage of methacrolein | Selectivity percentage of methacrylic acid |
|---|---|---|---|---|---|---|---|
| | Mo | P | Ca | Sn | | | |
| 17 | 12 | 1 | 1 | 2 | 350 | 75.2 | 72.1 |
| 18 | 12 | 0.5 | 0.5 | 1 | 350 | 62.4 | 74.0 |
| 19 | 11 | 1 | 0.5 | 0.5 | 330 | 71.3 | 71.9 |

COMPARISON EXAMPLES 7 and 8

The same procedures as those in Example 1 were carried out three times, except that the calcium ingredient was not employed, oxidation catalysts having the Table 1

| Example No. | | Atomic ratio of catalytic ingredient element atoms | | | | | | | Oxidation temperature (° C) | Contact period of time Second | Reaction percentage of methacrolein | Selectivity percentage of methacrylic acid |
|---|---|---|---|---|---|---|---|---|---|---|---|---|
| | | Mo. | P | Ca | Ta | Bi | As | Sb | Nb | | | | |
| Example | 2 | 12 | 1 | 1 | 1 | — | — | — | — | 320 | 1.7 | 62.0 | 74.3 |
| | 3 | 12 | 1 | 1 | — | 1 | — | — | — | 330 | 1.7 | 65.9 | 72.8 |
| | 4 | 12 | 1 | 0.5 | — | — | 0.5 | — | — | 300 | 1.7 | 66.0 | 81.5 |
| | 5 | 12 | 1 | 1 | — | 0.3 | — | — | — | 300 | 3.4 | 60.5 | 70.3 |
| | 6 | 12 | 1 | 0.5 | — | — | 1 | 1 | — | 290 | 3.4 | 69.8 | 77.1 |
| | 7 | 12 | 1 | 0.5 | — | 0.3 | — | 0.7 | — | 300 | 3.4 | 63.3 | 75.7 |
| | 8 | 13 | 1.5 | 2 | — | 0.8 | 1 | — | — | 300 | 3.4 | 65.3 | 73.5 |
| | 9 | 12 | 1 | 1 | 1 | — | — | 1 | — | 300 | 3.4 | 60.4 | 75.2 |
| | 10 | 12 | 1 | 1 | — | 1 | 1 | — | 1 | 330 | 1.7 | 64.3 | 70.5 |
| | 11 | 12 | 1 | 1 | 0.5 | — | 0.5 | 0.5 | 0.5 | 330 | 1.7 | 68.3 | 71.8 |
| | 12 | 12 | 1 | 1 | — | — | 0.1 | — | — | 330 | 1.7 | 65.1 | 76.8 |
| Comparison Example | 1 | 12 | 1 | 1 | — | — | — | — | — | 330 | 1.7 | 50.0 | 67.5 |
| | 2 | 12 | 1 | — | 2 | — | — | — | — | 310 | 1.7 | 51.9 | 60.7 |
| | 3 | 12 | 1 | — | — | — | — | — | — | 330 | 1.7 | 55.2 | 55.0 |
| | 4 | 12 | 1 | — | — | — | — | — | 1 | 300 | 1.7 | 60.4 | 59.1 |
| | 5 | 12 | 1 | — | — | 1 | — | — | — | 300 | 1.7 | 59.3 | 57.8 |
| | 6 | 12 | 1 | — | — | — | 1 | — | — | 330 | 1.7 | 40.6 | 70.2 |

EXAMPLE 13

Procedures identical to those in Example 1 were carried out, except that 6.03 g of stannic oxide were used in place of the titanium dioxide, and the atomic ratio of Mo:P:Ca:Sn was 12:1:1:1.

As a result of the oxidation procedures, the reaction percentage of methacrolein was 67.3 and the selectivity percentage of the resultant methacrylic acid was 75.1.

EXAMPLES 14 THROUGH 16

The same procedures as those in Example 1 were carried out three times, except that the atomic ratio of Mo:P:Ca:Ti and the oxidation temperature were as indicated in Table 2. The results are also indicated in Table 2.

Table 2

| Item Ex. No. | Atomic ratio | | | | Oxidation temp. (° C) | Reaction percentage of methacrolein | Selectivity percentage of methacrylic acid |
|---|---|---|---|---|---|---|---|
| | Mo | P | Ca | Ti | | | |
| 14 | 12 | 1 | 1 | 2 | 350 | 65.2 | 74.8 |
| 15 | 12 | 0.5 | 0.5 | 1 | 350 | 64.3 | 75.3 |
| 16 | 11 | 1 | 0.5 | 0.5 | 330 | 70.3 | 72.9 | atomic ratio of the catalytic ingredient elements as indicated in Table 4 were used. The oxidation catalyst used were outside the scope of the present invention. The results are also indicated in Table 4.

Table 4

| Item Comp. Ex. No. | Atomic ratio | | | | | Oxidation temp. (° C) | Reaction % of methacrolein | Selectivity % of methacrylic acid |
|---|---|---|---|---|---|---|---|---|
| | Mo | P | Ca | Sn | Ti | | | |
| 7 | 12 | 1 | — | 1 | — | 350 | 100 | 15.8 |
| 8 | 12 | 1 | — | — | 1 | 350 | 42.3 | 54.0 |

EXAMPLE 20

Procedures identical to those in Example 1 were repeated, except that 0.28 g of boric acid ($H_3BO_3$) and 0.54 g of antimony trioxide were employed instead of the titanium dioxide, the atomic ratio of Mo:P:Ca:B:Sb was 12:1:1:0.1:0.1, and the oxidation temperature was 330° C. As a result of the oxidtion procedure, the reaction percentage of methacrolein was 71.8 and the selectivity percentage of the resultant methacrylic acid was 81.1. Small amounts of acetic acid, carbon dioxide and carbon monoxide were by-produced in addition to the methacrylic acid.

EXAMPLE 21 through 28

Procedures identical to those in Example 1 were carried out, except that the oxidation catalysts had the atomic ratios of the ingredient elements indicated in Table 5, and the oxidation was carried out at the temperatures indicated in Table 5. In the preparation of the oxidation catalyst, the sources of the molybdenum, phosphorus, boron, calcium, antimony, magnesium, tantalum and arsenic ingredients employed were respectively ammonium molybdate, phosphoric acid, boric acid, calcium nitrate, antimony trioxide, magnesium nitrate, tantalum pentoxide and arsenic pentoxide. The results are indicated in Table 5.

In order to prepare an oxidation column, a U-shaped glass reaction tube having an inner diameter of 11 mm was filled with 25 ml of the oxidation catalyst.

A reaction feed consisting of 1.5% by volume of methacrolein in vapor phase. 10.0% by volume of oxygen, 31.0% by volume of steam and 57.5% by volume of nitrogen was flowed through the oxidation column at a flow rate of 176 ml/min at a temperature of 280° C, so that the reaction feed was kept in contact with the oxidation catalyst for 8.5 seconds.

The reaction percentage of the methacrolein was 86.9 and the selectivity percentage of the methacrylic acid was 81.3. Small amounts of acetic acid, carbon dioxide and carbon monoxide erere by-produced in addition to methacrylic acid.

Table 5

| Item Example No. | Atomic ratio | | | | | | | | Oxidation temperature (° C) | Contact period of time (second) | Reaction percentage of methacrolein | Selectivity percentage of methacrylic acid |
|---|---|---|---|---|---|---|---|---|---|---|---|---|
| | Mo | P | B | Ca | Mg | As | Sb | Ta | | | | |
| 21 | 12 | 1 | 0.5 | 1 | — | — | 0.5 | — | 330 | 3.4 | 78.1 | 76.5 |
| 22 | 12 | 1 | 0.1 | 1 | — | 0.1 | — | — | 330 | 1.7 | 80.8 | 79.0 |
| 23 | 12 | 1 | 0.5 | 0.5 | — | 0.5 | — | — | 350 | 1.7 | 85.2 | 72.3 |
| 24 | 12 | 1 | 0.5 | 1 | — | — | — | 0.5 | 330 | 1.7 | 75.6 | 74.9 |
| 25 | 12 | 1 | 0.1 | 0.5 | — | 0.1 | 0.05 | — | 330 | 3.4 | 71.9 | 80.7 |
| 26 | 13 | 1 | 0.2 | 1 | — | 0.5 | — | 0.5 | 350 | 1.7 | 86.4 | 74.3 |
| 27 | 12 | 1 | 2 | 1 | — | 1 | — | — | 350 | 1.7 | 81.5 | 79.8 |
| 28 | 12 | 1 | 0.5 | 0.5 | 0.5 | 0.5 | — | — | 350 | 1.7 | 76.3 | 81.3 |

COMPARISON EXAMPLE 9

The same procedures as those in Example 20 were carried out, except that the oxidation catalyst consisted of oxides of molybdenum, phosphorus and boron in an atomic ratio of Mo : P : B of 12 : 1 : 1 and the oxidation operation was carried out at a temperature of 320° C. The oxidation catalyst used was outside the scope of the present invention. The results of the oxidation had a high reaction percentage of methacrolein of 91.4 and a low selectivity percentage of the resultant methacrylic acid of 52.8.

EXAMPLE 29

A muddy aqueous suspension was prepared by dissolving 84.75 g of ammonium molybdate into 200 ml of water which had been heated to a temperature of 60° C and, then, adding 5.52 g of phosphoric acid, 9.45 g of calcium nitrate and 0.84 g. of arsenic trioxide into the solution in the above-mentioned order. The muddy aqueous suspension was concentrated at a temperature of 80 while stirring. The concentrated suspension was further concentrated by a drum dryer and, thereafter, completely dried at a temperature of 120° C. The resultant solid material was formed into pellets having a diameter of 5 mm and a length of 5 mm. The pellets were calcined at a temperature of 380° C for 5 hours in atmospheric air. The resultant oxidation catalyst had an atomic ratio Mo:P:Ca:As of 12:1.2:1:0.2.

EXAMPLE 30

Procedures identical to those in Example 29 were carried out, except that the contact time of the reaction feed with the oxidation catalyst was 5.1 seconds and the oxidation temperature was 300° C. The reaction percentage of methacrolein and the selectivity percentage of methacrylic acid were 82.6 and 80.0, respectively.

EXAMPLES 31 THROUGH 35

Procedures identical to those in Example 29 were repeated five times, except that the respective oxidation catalyst had the atomic ratio of the catalytic ingredient elements indicated in Table 6, and the respective oxidation temperature and the respective contact time of the reaction feed with the oxidation catalyst were as indicated in Table 6. In the preparation of the oxidation cataylsts, the sources of molybdenum, phosphorus, calcium, antimony, arsenic and boron ingredients employed were respectively ammonium molybdate, phosphoric acid, calcium nitrate, antimony trioxide, arsenic trioxide and boric acid.

The oxidation catalyst pellets were crushed into grains and screened to collect the grains having a 16 through 28 mesh size (Tyler standard). The grains in an amount of 5 ml were charged into a U-shaped glass reaction tube having an inner diameter of 6 mm.

The results are indicated in Table 6.

Table 6

| Item Ex. No. | Atomic ratio | | | | | | Oxidation temp. ° C | Contact period of time (second) | Reaction percentage of methacrolein | Selectivity percentage of methacrylic acid |
|---|---|---|---|---|---|---|---|---|---|---|
| | Mo | P | Ca | As | Sb | B | | | | |
| 31 | 12 | 1.2 | 0.1 | 0.2 | — | — | 355 | 1.7 | 96.2 | 76.3 |
| 32 | 12 | 2 | 0.2 | 0.1 | — | — | 350 | 1.7 | 93.6 | 69.1 |
| 33 | 12 | 1 | 0.01 | 0.05 | 0.05 | — | 350 | 1.7 | 96.9 | 68.9 |
| 34 | 12 | 1 | 1 | 0.1 | — | 0.1 | 330 | 3.4 | 90.3 | 78.0 |
| 35 | 12 | 1.2 | 1 | 0.2 | — | — | 340 | 3.4 | 95.6 | 83.1 |

What we claim is:

1. A method for the preparation of methacrylic acid by oxidation of methacrolein, comprising bringing a reaction feed containing methacrolein in vapor phase and molecular oxygen into contact at a temperature of 200°-450° C with an oxidation catalyst consisting of an oxide composition of the formula (I):

$$Mo_aP_bCa_cAs_dO_e \qquad (I)$$

wherein the subscripts $a$, $b$, $c$ and $d$ respectively denote the numbers of the respective element atoms, said numbers being within the ranges, $a = 5$ to $15$, $b = 1$ to $3$, $c = 0.1$ to $3$, $d = 0.1$ to $3$, and the subscript $e$ represents the number of oxygen atoms which corresponds to the oxides formed from the above mentioned elements and satisfies the average valency of the elements, said number $e$ being within the range of 16 to 60.

2. A method according to claim 1, wherein said oxidation catalyst is prepared by providing an aqueous liquid containing therein a molybdenum-containing compound, a phosphorus-containing compound, a calcium-containing compound and an arsenic compound liquid to form a solid material, and; calcining the dried solid material at a temperature of 300° to 500° C.

3. A method according to claim 1, wherein said oxidation catalyst is supported on a carrier selected from the group consisting of diatomaceous earth, silica, alumina, silicon carbide, silica-alumina and water-soluble silica sol.

4. A method according to claim 1, wherein said oxidation catalyst is in a fixed bed.

5. A method for the preparation of methacrylic acid by oxidation of methacrolein, comprising bringing a reaction feed containing methacrolein in vapor phase and molecular oxygen into contact at a temperature of 200°-450° C with an oxidation catalyst consisting of an oxide composition of the formula (II):

$$Mo_aP_bCa_cAs_fY_gO_e \qquad (II)$$

wherein Y represents at least one member selected from the group consisting of antimony, niobium and magnesium atoms, the subscripts $a$, $b$, $c$, $f$ and $g$ respectively denote the numbers of the respective element atoms, said numbers being within the ranges, $a = 5$ to $15$, $b = 1$ to $3$, $c = 0.1$ to $3$, $f = 0.1$ to $3$ and $g = 0.1$ to $3$, and the subscript $e$ represents the number of oxygen atoms which corresponds to the oxides formed from the above mentioned elements and satisfies the average valency of the elements, said number $e$ being within a range of 16 to 68.

6. A method according to claim 5, wherein said oxidation catalyst is prepared by providing an aqueous liquid containing therein a molybdenum-containing compound, a phosphorus-containing compound, a calcium containing compound, an arsenic compound and at least one compound selected from the group consisting of antimony-, niobium- and magnesium-containing compounds; evaporating the aqueous liquid to form a solid material and; calcining the dried solid material at a temperature of 300° to 500° C.

7. A method for the preparation of methacrylic acid by oxidation of methacrolein, comprising bringing a reaction feed containing methacrolein in vapor phase and molecular oxygen into contact at a temperature of 200°- 450° C with an oxidation catalyst consisting of an oxide composition of the formula (III):

$$Mo_aP_bCa_cAs_hZ_iO_e \qquad (III)$$

wherein Z represents at least one member selected from the group consisting of bismuth, tin, titanium, tantalum, boron, antimony, niobium and magnesium atoms, the subscripts $a$, $b$, $c$, $h$ and $i$ respectively represent the numbers of the respective element atoms, said numbers being within the following ranges, $a = 5$ to $15$, $b = 1$ to $3$, $c = 0.1$ to $3$, $h = 0.1$ to $3$, and $i = 0.1$ to $3$, and the subscript $e$ represents the number of oxygen atoms which correspond to the oxides formed from the above mentioned elements and satisfies the average valency of the elements involved, the number $e$ being within a range of 16 to 68.

8. A method according to claim 7, wherein said oxidation catalyst is prepared by providing an aqueous liquid containing therein a molybdenum-containing compound, a phosphorus-containing compound, a calcium-containing compound, an arsenic-containing compond and at least one compound selected from the group consisting of bisumth-, tin-, titanium-, tantalum-, boron-, antimony-, niobium- and magnesium-containing compounds; evaporating said aqueous solution to form a solid material and; calcining the dried solid material at a temperature of 300° to 500° C.

9. A method according to claim 7, wherein said Z in the formula (III) is a boron atom.

10. A method according to claim 7, wherein said Z in the formula (III) is an antimony atom.